United States Patent [19]

Hasselberg

[11] Patent Number: 5,272,061
[45] Date of Patent: Dec. 21, 1993

[54] ASSAY FOR SERUM CHOLINESTERASE ACTIVITY

[75] Inventor: Stephen C. Hasselberg, Rochester, N.Y.

[73] Assignee: Eastman Kodak Company, Rochester, N.Y.

[21] Appl. No.: 763,383

[22] Filed: Sep. 20, 1991

[51] Int. Cl.$^5$ .............................................. C12Q 1/46
[52] U.S. Cl. .......................................... 435/20; 435/4; 435/805; 435/810; 436/801; 436/807; 436/170; 436/63; 422/61
[58] Field of Search ................... 435/200, 805, 810; 436/801, 807, 170, 63; 422/61

[56] References Cited

U.S. PATENT DOCUMENTS

| | | | |
|---|---|---|---|
| 3,992,158 | 11/1976 | Przybylowicz et al. | 23/253 TP |
| 4,042,335 | 8/1977 | Clement | 23/253 TP |
| 4,144,306 | 3/1979 | Figueras | 422/56 |
| 4,258,001 | 3/1981 | Pierce et al. | 422/56 |
| 4,357,363 | 11/1982 | Pierce et al. | 427/2 |
| 4,929,545 | 5/1990 | Freitag | 435/11 |
| 4,978,615 | 12/1990 | Aoyama et al. | 435/25 |

OTHER PUBLICATIONS

Hasselberg et al., *Clinical Chemistry*, vol. 35(6), Jul. 1989, p. 1120.

Thomsen T., et al., *Estimation of Cholinesterase Activity (EC 3.1.1.7;3.1.1.8) in Undiluted Plasma and Erythrocytes as a Tool for Measuring In Vivo Effects of Reversible Inhibitors, J. Clin. Chem. Clin. Biochem.*, vol. 26, pp. 469–475 (1988).

Schmidt E., et al., *Proposal for Standard Methods for the Determination of Enzyme Catalytic Concentrations in Serum and Plasma at 37° C.$^1$), J. Clin. Chem. Clin. Biochem.*, vol. 28, pp. 805–808 (1990).

*Primary Examiner*—Ronald W. Griffin
*Assistant Examiner*—Pamela S. Webber
*Attorney, Agent, or Firm*—John R. Everett

[57] ABSTRACT

A dry analytical element for the determination of serum cholinesterase (CHE) activity is disclosed. The element analyses undiluted body fluids and employs butyrylthiocholine as the substrate for CHE. Butyrylthiocholine is hydrolyzed by serum cholinesterase and liberates butyric acid and thiocholine. The thiocholine liberated then reduces ferricyanide to ferrocyanide and the rate of change is measured by reflectance densitometry.

15 Claims, 2 Drawing Sheets

ASSAY FOR SERUM CHOLINESTERASE ACTIVITY

BACKGROUND OF THE INVENTION

1. Field of the Invention

This invention relates generally to diagnostic tests to determine the activity of serum cholinesterase. More particularly, the invention concerns a dry element and a method for determining serum cholinesterase activity in undiluted aqueous liquids.

2. Description of Related Art

The determination of the activity of serum cholinesterase (CHE) is important in the early diagnosis of various disease states such as degenerative liver disorders and poisoning caused by toxic agents such as insecticides and herbicides containing carbamates or organic phosphoric acid esters. These compounds inhibit CHE, thus a reduced level of CHE activity in a patient's serum might be diagnostic of chemical poisoning. In the case of carbamate pesticides, the inhibitory effect of these toxic agents might be reversed and cholinesterase activity restored if, for example, the patient's serum is diluted and the concentration of the toxic agent in the test reagent is lowered. In such cases, in vitro measurement of CHE activity in diluted samples might not truly reflect the severity of the in vivo state.

In determining the activity of CHE in serum it is customary to predilute the test serum sample because the level of CHE activity normally present in human sera is very high. Because such dilution could reverse CHE inhibition by toxic agents, it would be preferred to employ a method that is capable of determining a range of CHE activity without prior dilution of the test samples. One such method has been disclosed by Thomsen, Kewitz and Pleul, J. Clin. Chem. Clin. Biochem, vol.26-/No.7, p.469-475 (1988). That method, however, employs a manual technique that uses reagents in wet solution and is therefore not as convenient or reproducible as automated methods or methods using dry analytical elements. Further, the reagents include radioactive labelled acetylcholine and thereby present certain known hazards.

It would be desirable to have a dry, analytical element for determining serum cholinesterase activity in undiluted aqueous liquids such as biological fluids.

SUMMARY OF THE INVENTION

Accordingly, the object of this invention is to provide a dry type analytical element for CHE assay of diluted and undiluted aqueous liquids such as body fluids. Briefly summarized, according to one aspect of the invention, there is provided a method for assaying serum cholinesterase activity in an aqueous liquid comprising the steps of:

A) contacting a sample of the aqueous liquid with an analytical element for assaying serum cholinesterase activity comprising a support having thereon at least one layer, wherein the element also comprises:
  a) butyrylthiocholine;
  b) ferricyanide at a coverage of about 0.02 to 2.0 g/m$^2$;
  c) a binder material at a coverage of about 3 to 12 g/m$^2$; and
  d) a buffer to establish a pH in the range of about 7.0–8.5; and B) monitoring the rate of change in reflectance density to assay the activity of serum cholinesterase in the sample.

In another aspect of the invention, there is provided the analytical element described in the above method for assaying serum cholinesterase activity.

One advantageous feature of this invention is that the test can be performed with undiluted serum, thereby avoiding recovery of enzyme activity upon dilution.

Another advantageous feature is that the element of this invention is useful in automated analyzers and thereby minimizes the risk of error or inconsistency.

Yet another advantage of this invention is that the chemistry is "dry" and offers greater handling and storage convenience than the "wet" approach.

The assay provided by the invention is non-enzymatic and therefore provides better reagent stability and cost advantage than comparable enzymatic tests. By "non-enzymatic" it is meant that no enzyme is present in the element according to the invention although CHE might be present in the sample.

In order to provide a dry analytical element for assaying CHE in undiluted aqueous liquids, several problems had to be overcome. It was particularly difficult to define the amount of ferricyanide to be incorporated in the dry element of the invention because of the very broad range of CHE found in undiluted human serum. The amount of ferricyanide is critical because if too much is present in the web, the initial density will be too high and a reading cannot be made. If too little is present, the ferricyanide will be exhausted before the endpoint of the reaction is reached and again an accurate reading cannot be made. Prior art methods overcome this problem by diluting samples with very high CHE levels; but there are problems involved with dilution, as discussed above.

We discovered through research that the range of ferricyanide which functions optimally as an indicator of CHE activity in a dry element depends on the concentration of the other constituents in the web, especially the binder material, e.g. gelatin. We have found that the useful range of ferricyanide in the element is about 0.2 to about 2.0 g/m$^2$ and the useful range of binder material that is operable with the above stated range of ferricyanide is about 3 to about 12 g/m$^2$. One skilled in the art would be able to arrive at the optimum concentrations within these ranges that are suitable for particular assays. We are aware of no teaching that the amount of binder material in the web would overcome the problem described above. It was unexpected that a dry element could be made to determine the very broad range of CHE activity in undiluted human sera.

Another problem unexpectedly solved by the invention is interference by bilirubin, a natural constituent of serum. It is known that the natural yellow pigment in bilirubin causes a bias in the density reading. Because this invention assays undiluted serum, the system gets the full brunt of bilirubin interference. We overcome this problem and obtain accurate results by reducing the amount of gel cross-linking. We used a small amount of hardener (for example about 0.02 to about 2 g/m$^2$ BVSME). Some cross-linking is needed, however, so BVSME could not be totally excluded.

Another unexpected result obtained by the invention is that coating-to-coating reproducibility is greatly improved when an anionic surfactant, preferably Olin 10G TM, defined below, is incorporated in the layers containing the reagents.

DETAILS OF THE INVENTION

Figure 1:
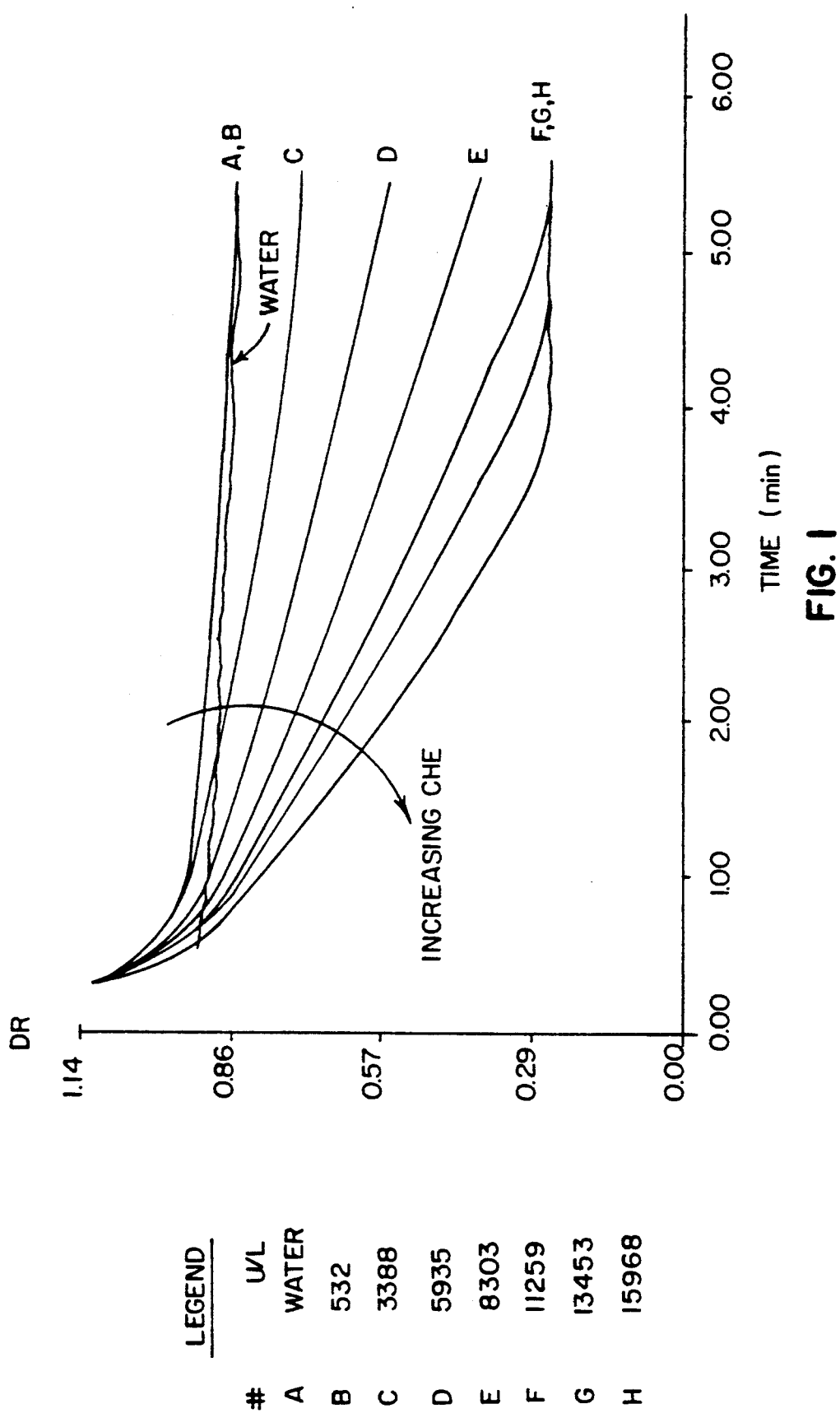
FIG. 1 is a graph of kinetic traces of density versus time, showing that the negative slope of the kinetic trace increases with increasing CHE activity.

As used herein, the term "fluid contact" and similar terms refer to zones or layers of an element which are associated with one another in a manner such that, under conditions of use, a fluid, whether liquid or gaseous, can pass in the element between these layers or zones. Such fluid contact therefore refers to the capability of the element to permit passage of at least some components of a fluid sample between zones or layers of the element which are said to be in "fluid contact". Zones which are in fluid contact can be contiguous, but they also may be separated by intervening zones or layers. Such intervening zones or layers however will also be in fluid contact in this case and will not prevent the passage of fluid between the fluid contacting layers or zones.

The term "dry" as used herein to describe analytical methods refers to analytical methods and techniques that are carried out using chemical reagents contained in various "dry-to-the-touch" test elements such as "dip and read" test strips, multilayer test elements and the like. "Dry" methods require no liquid for reconstitution or analysis.

The term "dry coverage" as used herein indicates that the coating coverage is determined as "dry weight" after normal coating and drying processes.

The term "porous" as used herein means being full of pores such that a fluid can be absorbed by capillary action and can pass to other layers in fluid contact with the porous layer.

The term "reflective" as used herein means that incident light applied to the element would not be transmitted through the element but would be reflected back to a photodetector where the reflected density can be measured.

The chemical basis for this assay is that butyrylthiocholine is hydrolyzed by CHE and liberates butyric acid and thiocholine. The thiocholine liberated then reduces ferricyanide to ferrocyanide and the rate of change from ferricyanide to ferrocyanide is measured by reflectance densitometry. Measurement is possible because ferricyanide has an absorption maximum at 405 nm, while ferrocyanide has little absorption at this wavelength. The level of cholinesterase activity is then directly correlated to the rate of change in absorbance.

The above-described series of chemical reactions are carried out on an automatic analyzer, such as the EKTACHEM TM analyzer, using the dry analytical element of the invention spotted with a sample to be assayed for CHE activity. The dry analytical elements useful for the assay of liquids can be prepared according to the teachings of U.S. Pat. No. 3,992,158 and U.S. Pat. No. 4,357,363 the contents of which are incorporated herein in their entirety.

Briefly described, the analytical element of this invention comprises one or more layers coated on a suitable support. If the element contains more than one layer (a multilayer element), the layer most adjacent to the support is a reagent layer upon which one or more additional reagent layers may be superposed. Any or all reagent layers may contain the constituents butyrylthiocholine or ferricyanide. Optionally, both of these constituents may be in the same reagent layer. In a multilayer element of the type described, the layer most distant from the support is a spreading layer that receives and distributes the aqueous liquid to be assayed for CHE. The spreading layer may also contain the constituents butyrylthiocholine or ferricyanide, or both. A buffer is essential to the element and may be included in any or all layers of the element. Optionally, all constituents of the element may be in a single layer. Whether contained in the same or in different layers of the element, all constituents must be in fluid contact with each other, meaning that reagents and reaction products can pass within a layer and between superposed regions of adjacent layers.

The support can be any suitable dimensionally stable, and preferably, nonporous and transparent (i.e. radiation transmissive) material which transmits electromagnetic radiation of a wavelength between about 200 and about 900 nm. A radiation-transmissive support is particularly preferred to enhance and facilitate determination of detectable changes occurring in these elements by use of various radiation detection methods. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

A reagent layer is coated on the support. The reagent layer can contain the indicator composition comprising one or more reagents (for example, ferricyanide or ferricyanide and butyrylthiocholine) dispersed in one or more synthetic or natural binder materials, such as gelatin or other naturally-occurring colloids, as well as different synthetic hydrophilic polymers such as poly(acrylamide), poly(vinylpyrrolidone), poly(acrylamide-co-N-vinyl-2-pyrrolidone), copolymers of the above, and polymers or copolymers to which crosslinkable monomers have been added.

The reagent layer can contain a buffer, essential to the invention. Useful buffers include phosphate, pyrophosphate, tris(hydroxymethyl)aminomethane (TRIS), 2{[tris(hydroxymethyl)methyl]amino}-1-ethanesulfonic acid (TES) and other buffers with pH in the range of 7.0 to 8.5. The buffer may be included in any or all of the layers described above, or it may be in a separate layer devoid of ferricyanide and butyrylthiocholine.

Several anionic surfactants such as Olin-10G TM, TX-405 TM, Zonyl FSN TM (a family of octylphenoxy polyethoxy ethanol nonionic surfactants sold by Rohm and Haas), etc. may optionally be included in the reagent layer. Several different cross-linking agents are also optional, such as bisvinylsulfonylmethane, gluteraldehyde, etc.

The spreading layer is a porous, reflective layer to uniformly distribute the liquid test sample over the element. The spreading layer may contain the constituents butyrylthiocholine or ferricyanide or both. Materials for use in spreading layers are well known in the art of making dry analytical elements as disclosed, for example, in U.S. Pat. No. 4,258,001 and the above cited patents.

An exemplary spreading layer is presented in Table 1 below. Pigments other than barium sulfate could be used, for example, titanium dioxide. Binders other than cellulose acetate could be used, for example, various polyurethanes and other polymers. Surfactants other than TX-405 TM could be used, for example, TX-100 TM. Halide ions other than the iodide could be used, for example butyrylthiocholine chloride. In addition, other thiocholines, such as acetyl or propionylthiocholine could be used instead of butyrylthiocholine.

Other optional layers, e.g. subbing layers, radiation-blocking layers, etc. can be included if desired. The layers of the element can contain a variety of other desirable but optional components, including surfactants, thickeners, buffers, hardeners, antioxidants, coupler solvents, and other materials known in the art. The amounts of these components are also within the skill of a worker in the art.

Changes in the element can be detected with suitable spectrophotometric apparatus, usually a reflectometer, using generally known procedures disclosed, for example, in U.S. Pat. No. 3,992,158 at Cols. 14–15 and U.S. Pat. No. 4,357,363 at Cols. 27. In an enzymatic reaction, the resulting product is determined by measuring, for example, the rate of change of reflection or transmission density in a finite area of the element of the invention contacted with the assay sample. The area measured is generally from about 3 to about 5 mm.

A representative element of this invention is presented below. It will be understood by those skilled in the art that the principle of the present invention can be usefully incorporated into any analytical element employing the method provided by the present case. It will also be understood that CHE activity in other samples besides sera can also be assayed using this element.

TABLE 1

| Immunoassay Element of the Invention | | | |
|---|---|---|---|
| | | Dry Coverage (g/m$^2$) | |
| | | Most Preferred | Useful Range |
| Spreading/ Reagent Layer | BaSO$_4$ | 105.6 | 80–250 |
| | Cellulose Acetate | 10.1 | 5–150 |
| | TX-405 TM | 2.1 | 0.5–10 |
| | Butyrylthiocholine Iodide | 2.9 | 0.5–5 |
| | Polyurethane | 1.1 | |
| Subbing Layer (optional) | Poly-N-isopropylacrylamide | | 0.59 |
| Gelatin/ Reagent Layer | Gelatin | 6.46 | 3–12 |
| | KH$_2$PO$_4$ | 2.04 | 0.5–10 |
| | K$_3$Fe(CN)$_6$ | 1.45 | 0.2–5 |
| | TX-100 TM | 0.54 | 0.001–2 |
| | Bisvinylsulfonylmethylether | 0.05 | 0.02–2 |

The names and symbols used in the above element and text have the following meanings:

| Zonyl FSN TM: | A nonionic, fluorinated surfactant sold by E. I. du Pont de Nemours. |
| TX-100 TM | A family of octylphenoxy polyethoxy |
| TX-405 TM | ethanol nonionic surfactants sold by |
| Olin-10G TM: | Rohm and Haas. |
| BVSME: | Bis (vinylsulfonylmethyl) ether gelatin hardener. |

The reagent layer was coated on a subbed, gelatin washed poly(ethylene terephthalate) support, and the spreading layer was coated over the reagent layer. All of the aforementioned layers were coated using conventional coating techniques known in the art for making dry assay elements mentioned above such as those disclosed in U.S. Pat. No. 4,357,363 and U.S. Pat No. 3,992,158.

The element of the invention is intended for use with serum or plasma samples but any fluid that sufficiently mimics serum could also be used. These include typical control and proficiency fluids.

No special sample preparation is required other than the separation of serum or plasma from whole blood. Dilution is not required, but is allowed provided the diluted activity is sufficient to be read. The samples can be frozen and maintain activity for long periods of time. They should be thawed and allowed to reach room temperature prior to assay.

The assay of the invention utilizes between about 5 and 20 μL of sample. Although the invention allows for variations in the volume of applied samples, about 11 μL is preferred. Different calibration curves are required for the different sample volumes. Physical contact is made between the liquid sample under analysis and the analytical element. Such contact can be accomplished in any suitable manner, preferably by spotting the element by hand or machine with a drop of the sample on the spreading layer with a suitable dispensing means.

After sample application, the element is exposed to any conditioning, such as incubation heating or the like, that may be desirable to quicken or otherwise facilitate chemical reaction. Such conditioning is preferably performed at 25°–40° C., most preferably at 37° C. The element is monitored for any change in reflectance density during the period of conditioning, usually for about 3 to about 7 minutes, preferably for about 5 minutes, although changes may occur as soon as about 20 to about 25 seconds, or as long as 30 to 60 minutes.

The method of determining the CHE activity is illustrated by the examples below. The analytical element used in all the examples is that shown in Table 1 herein.

EXAMPLE 1

Calculating the Rate of Change (Dr/Min) Using Samples With Known Concentrations of CHE The operability of the invention in testing for CHE activity is demonstrated as follows. A pool of human serum was treated with acid to destroy endogenous CHE activity and then spiked with horse CHE to provide a series of fluids with CHE activity of 532, 3388, 5935, 8303, 11259, 13453 and 15968 U/L. CHE activities of the above 7 samples were determined by the butyrylthiocholine/Ellman's reagent method. This method has been designated by the British Association of Clinical Biochemists as a reference method. (*Proposed Methods for Determination of Some Enzymes in Blood Serum.* News Sheet Assoc. Clin. Biochem., 202, 31s (1980)).

The above fluids and water, were all spotted on the element of Table 1 and assayed for CHE activity on the EKTACHEM TM 700 analyzer according to the procedure described above. Reflectance density (Dr) at 400 nm was monitored during a 5 minute incubation at 37° C. and the rate of change in Dr determined by the analyzer. Suitable detection apparatus and procedures are known in the art.

Kinetic traces of reflectance density versus time are shown in FIG. 1. This shows that the negative slope of the Kinetic trace (Dr/min) increases with increasing CHE activity.

The rate (Dr/min) was determined by linear regression through the linear region of the density curve.

EXAMPLE 2

Assaying Test Samples on the Element of the Invention

Figure 2:
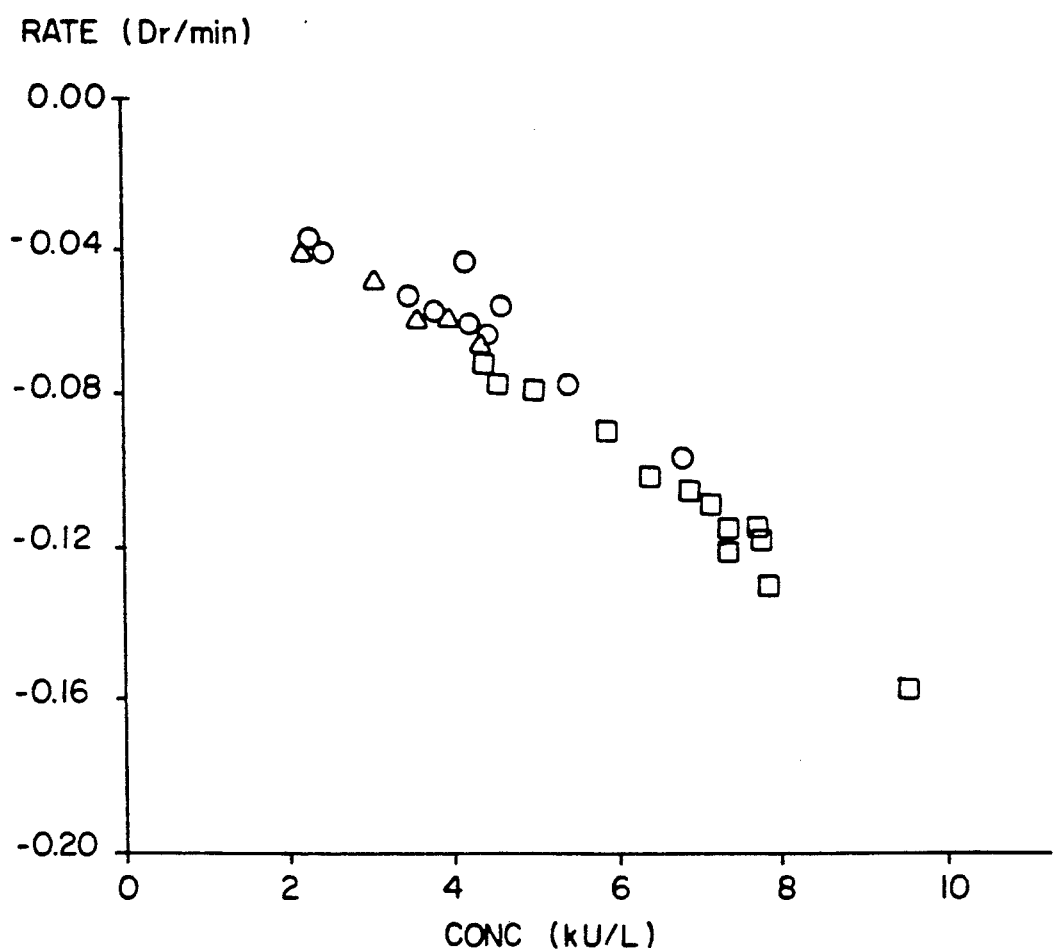
FIG. 2 is a graph showing results of assays of patient serum samples using an EKTACHEM TM 700 clinical chemistry analyzer. This shows that results obtained using the method of the invention corresponds well with results obtained using a reference method for assaying CHE activity.

Thirty-five patient samples were obtained; 15 from apparently healthy individuals, 10 from individuals showing signs of liver dysfunction (high bilirubin), 10 from pesticide applicators. All of these samples were assayed for CHE activity by the above mentioned Ellman's reagent technique. They were then spotted on the element of the invention and assayed using an EKTACHEM TM 700 analyzer. The slope of the linear region of the Kinetic curve was calculated (Dr/min) as described above. This was plotted against the concentration (activity) as reported by the reference method. The results are shown in FIG. 2.

As these samples generally fall on one curve, we see that this technique can be correlated to and even calibrated by the aforementioned reference (butyrylthiocholine/Ellman's reagent) method.

The invention has been described in detail with particular reference to certain preferred embodiments thereof, but it will be understood that variations and modifications can be effective within the spirit and scope of the invention.

I claim:

1. A method for assaying serum cholinesterase activity in an aqueous liquid comprising the steps of:
    A) contacting a sample of the aqueous liquid with an analytical element for assaying serum cholinesterase activity comprising a support having thereon at least one layer, wherein the element also comprises:
        a) butyrylthiocholine;
        b) ferricyanide at a coverage of about 0.02 to 2.0 $g/m^2$;
        c) a binder material at a coverage of about 3 to 12 $g/m^2$; and
        d) a buffer to establish a pH in the range of about 7.0–8.5; and
    B) monitoring the rate of change in reflectance density to assay the activity of serum cholinesterase in the sample.

2. The method according to claim 1 wherein the aqueous liquid is undiluted.

3. The method according to claim 1 wherein the preparation is monitored by reflectance densitometry at 375–450 nm.

4. A method according to claim 1 wherein the element comprises a support having thereon, in the following order;
    a) a reagent layer containing ferricyanide at a coverage of about 1.5 to 2.5 $g/m^2$, gelatin at a coverage of about 6 to 10 $g/m^2$ and a buffer to establish a pH in the range of 7.0–8.5; in fluid contact with
    b) a spreading layer containing butyrylthiocholine iodide.

5. The method according to claim 4 wherein the aqueous liquid is undiluted.

6. An analytical element for assaying serum cholinesterase activity comprising a support having thereon at least one layer, wherein the element also comprises:
    a) butyrylthiocholine;
    b) ferricyanide at a coverage of about 0.02 to 2.0 $g/m^2$;
    c) a binder material at a coverage of about 3 to 12 $g/m^2$; and
    d) a buffer to establish a pH in the range of about 7.0–8.5.

7. The element defined in claim 6 comprising one or more reagent layers and a spreading layer wherein (a), (b), (c) and (d) are located in
    i) one or more reagent layers;
    ii) one or more reagent layers and a spreading layer; or
    iii) the spreading layer.

8. The element of claim 7 comprising:
    a) one or more reagent layers containing a binder material at a coverage of about 3 to about 12 $g/m^2$ and at least one compound selected from the group consisting of butyrylthiocholine, ferricyanide at a coverage of about 0.02 to 2.0 $g/m^2$ and a buffer with a pH in the range of about 7.0–8.5; and
    (b) a spreading layer.

9. The element defined in claim 7 wherein the spreading layer contains one or more materials selected from the group consisting of butyrylthiocholine, ferricyanide at a coverage of about 0.02 to 2.0 $g/m^2$, a binder material at a coverage of about 3 to about 12 $g/m^2$, and a buffer with a pH in the range of about 7.0–8.5.

10. The element defined in claim 7 or 9 also comprising a hardener.

11. The element defined in claim 10 wherein the hardener is present at a coverage of between 0.02 and 2 $g/m^2$.

12. The element defined in claim 7, 8 or 9 also comprising an anionic surfactant at a coverage of about 0.001 to about 2 $g/m^2$.

13. The element defined in claim 7, 8 or 9 wherein the butyrylthiocholine is butyrylthiocholine iodide.

14. The element defined in claim 7, 8 or 9 wherein the binder material is gelatin.

15. The element of claim 7 comprising a support having thereon, in the following order;
    a) a reagent layer containing ferricyanide at a coverage of about 1.5 to 2.5 $g/m^2$, gelatin at a coverage of about 6 to 10 $g/m^2$ and a buffer to establish a pH in the range of 7.0–8.5; and in fluid contact with
    b) a spreading layer containing butyrylthiocholine iodide.

* * * * *